(12) United States Patent
Ye et al.

(10) Patent No.: US 12,129,517 B1
(45) Date of Patent: Oct. 29, 2024

(54) KIT FOR DETECTING AFRICAN SWINE FEVER VIRUS (ASFV)

(71) Applicant: Jiangxi Agricultural University, Nanchang (CN)

(72) Inventors: Yu Ye, Nanchang (CN); Ning Jiang, Nanchang (CN); Yuxin Tang, Nanchang (CN); Dongyan Huang, Nanchang (CN)

(73) Assignee: Jiangxi Agricultural University, Nanchang (CN)

( * ) Notice: Subject to any disclaimer, the term of this patent is extended or adjusted under 35 U.S.C. 154(b) by 0 days.

(21) Appl. No.: 18/629,793

(22) Filed: Apr. 8, 2024

(30) Foreign Application Priority Data

Sep. 8, 2023 (CN) .......................... 202311152326.1

(51) Int. Cl.
*C12Q 1/6844* (2018.01)
*C12Q 1/6876* (2018.01)
*C12Q 1/70* (2006.01)

(52) U.S. Cl.
CPC ......... *C12Q 1/6844* (2013.01); *C12Q 1/6876* (2013.01); *C12Q 1/70* (2013.01)

(58) Field of Classification Search
None
See application file for complete search history.

(56) References Cited

U.S. PATENT DOCUMENTS 11,060,149 B2    7/2021   Steelman

FOREIGN PATENT DOCUMENTS

| CN | 111235232 | 6/2020 |
| CN | 112359137 | 2/2021 |

OTHER PUBLICATIONS

Heather E. James et al. Detection of African swine fever virus by loop-mediated isothermal amplification. Journal of Virological Methods 164 (2010) 68-74.
Pan Xing et al., Advances in the application of CRISPR/Cas systems in the diagnosis of infectious diseases. International Journal of Laboratory Medicine. https://link.cnki.net/urlid/50.1176.R.20230804.1334.002 Abstract Only.
First Office Action by CNIPA, Chinese Patent Application No. 202311152326.1, issued on Oct. 19, 2023.
Second Office Action by CNIPA, Chinese Patent Application No. 202311152326.1, issued on Nov. 9, 2023.
Notification to Grant Patent Right for Invention by CNIPA, Chinese Patent Application No. 202311152326.1, issued on Dec. 6, 2023.
Loop-mediated isothermal amplification (LAMP)—review and classification of methods for sequencespecific detection. Lisa Becherer et al. Anal. Methods, 2020, 12, 717-746.

*Primary Examiner* — Young J Kim
(74) *Attorney, Agent, or Firm* — Fish IP Law, LLP

(57) ABSTRACT

The present disclosure provides a kit for detecting an African swine fever virus (ASFV), and provides a corresponding single guide RNA (sgRNA) with a nucleic acid sequence shown in any one of SEQ ID NO: 1 to SEQ ID NO: 5. The kit is based on loop-mediated isothermal amplification (LAMP)-clustered regularly interspaced short palindromic repeat (CRISPR)/Cas12b and can detect the ASFV in one tube at a constant temperature. The kit only needs to set one reaction temperature, does not open its lid midway, and has high sensitivity and specificity while showing no specificity to other swine viruses. The kit exhibits high efficiency and convenience, and does not rely on a large-scale experimental equipment. Compared with the traditional fluorescence quantitative PCR methods, the kit has a greatly improved sensitivity in detecting 1 copy/μL. The kit realizes visual detection by combining with colloidal gold test strip detection.

2 Claims, 9 Drawing Sheets
Specification includes a Sequence Listing.

a b c d e

KIT FOR DETECTING AFRICAN SWINE FEVER VIRUS (ASFV)

CROSS REFERENCE TO RELATED APPLICATION

This patent application claims the benefit and priority of Chinese Patent Application No. 202311152326.1, filed with the China National Intellectual Property Administration on Sep. 8, 2023, the disclosure of which is incorporated by reference herein in its entirety as part of the present application.

REFERENCE TO SEQUENCE LISTING

A computer readable XML file entitled "SEQUENCE LISTING", that was created on Feb. 23, 2024, with a file size of about 11192 bytes, contains the sequence listing for this application, has been filed with this application, and is hereby incorporated by reference in its entirety.

TECHNICAL FIELD

The present disclosure belongs to the technical field of nucleic acid detection, and in particular relates to a kit for detecting an African swine fever virus (ASFV).

BACKGROUND

Currently, clinical detection of African swine fever virus (ASFV) is mainly conducted through fluorescence quantitative PCR, which is time-consuming and relies on large instruments. Although loop-mediated isothermal amplification (LAMP), an isothermal amplification technology with a high sensitivity, has been approved for marketing, but is prone to false positives. In the existing technology, there is a detection method that fuses LAMP and clustered regularly interspaced short palindromic repeat (CRISPR) to improve the accuracy of detection results. However, the detection of LAMP combined with CRISPR in the existing technology still needs to be completed step by step so far. For example, in a reverse transcription (RT)-LAMP amplification system for visual detection of viral nucleic acid RNA disclosed in the patent CN112359137A, the amplification and cleavage reactions still need to be conducted gradually and are not convenient enough. Conventional immune colloidal gold test strips can conveniently and quickly visually detect the ASFV, but are not sensitive enough. Therefore, there is still a demand to explore a rapid method for detecting the ASFV for better application in the clinical detection.

SUMMARY

An objective of the present disclosure is to provide a kit for detecting an ASFV.

To achieve the above objective, the present disclosure provides the following technical solutions based on a LAMP-CRISPR/Cas12b technology:

The present disclosure provides a kit for detecting an ASFV based on LAMP-CRISPR/Cas12b, including: a single guide RNA (sgRNA) targeting an ASFV P1192R gene, a loop-mediated isothermal amplification (LAMP) amplification primer designed for the ASFV P1192R gene, AapCas12b, a single-stranded DNA (ssDNA) probe, a Bst2.0 polymerase, and a reaction buffer; where the sgRNA has a nucleic acid sequence shown in any one of SEQ ID NO: 1 to SEQ ID NO: 5.

In the present disclosure, the reaction buffer includes $MgSO_4$ and betaine.

Preferably, the $MgSO_4$ is used at a final concentration of 6 mM to 12 mM.

Preferably, the betaine is used at a final concentration of 0.1 M to 0.8 M.

Optionally, the ssDNA probe has a sequence of 5'-6-FAM-TTTTTTTTTTTT-BHQ1-3' shown in SEQ ID NO: 7.

The present disclosure further provides use of the kit in detecting an ASFV for a non-diagnostic purpose, including: mixing the sgRNA, the LAMP amplification primer, the AapCas12b, the ssDNA probe, the Bst2.0 polymerase, and the reaction buffer in the kit with a template to be tested to allow a reaction at a constant temperature of 55° C. to 60° C. for 30 min, and then reading an obtained reaction result through a fluorescence reading device.

Further, the kit further includes an immune colloidal gold test strip; and the ssDNA probe has a sequence of 5'-6-FAM-TTTTTTTTTTTT-Bio-3' shown in SEQ ID NO: 7.

In the present disclosure, the immune colloidal gold test strip is a lateral flow test strip; a conjugate pad includes a gold-labeled antibody capable of specifically binding to carboxyfluorescein (FAM); a test line is coated with an antibody, a protein, or avidin that is capable of binding to Bio; and a control line is coated with an antibody, a protein, or avidin that is capable of binding to the FAM.

The present disclosure further provides use of the kit in detecting an ASFV for a non-diagnostic purpose, including: mixing the sgRNA, the LAMP amplification primer, the AapCas12b, the ssDNA probe, the Bst2.0 polymerase, and the reaction buffer in the kit with a template to be tested to allow a reaction at a constant temperature of 55° C. to 60° C. for 30 min, and then adding an obtained reaction solution onto the immune colloidal gold test strip to allow color development.

The present disclosure has following beneficial effects:
(1) The present disclosure provides a sgRNA targeting an ASFV P1192R gene, where the sgRNA has an extremely strong collateral cleavage activity on a target sequence.
(2) In the present disclosure, the kit is based on CRISPR/Cas12b and can detect the ASFV in one tube at a constant temperature. The kit only needs to set one reaction temperature, does not open its lid midway, and has high sensitivity and specificity while showing no specificity to other swine viruses. The kit exhibits high efficiency and convenience, and does not rely on a large-scale experimental equipment.
(3) Compared with the traditional fluorescence quantitative PCR methods, the kit of the present disclosure has a greatly improved sensitivity in detecting 1 copy/μL.
(4) The present disclosure further provides a kit based on a visual colloidal gold test strip, which can be conveniently used in grassroots laboratories and breeding enterprises for grassroots epidemic monitoring and identification and diagnosis of African swine fever (ASF).

DETAILED DESCRIPTION OF THE EMBODIMENTS

Figure 1:
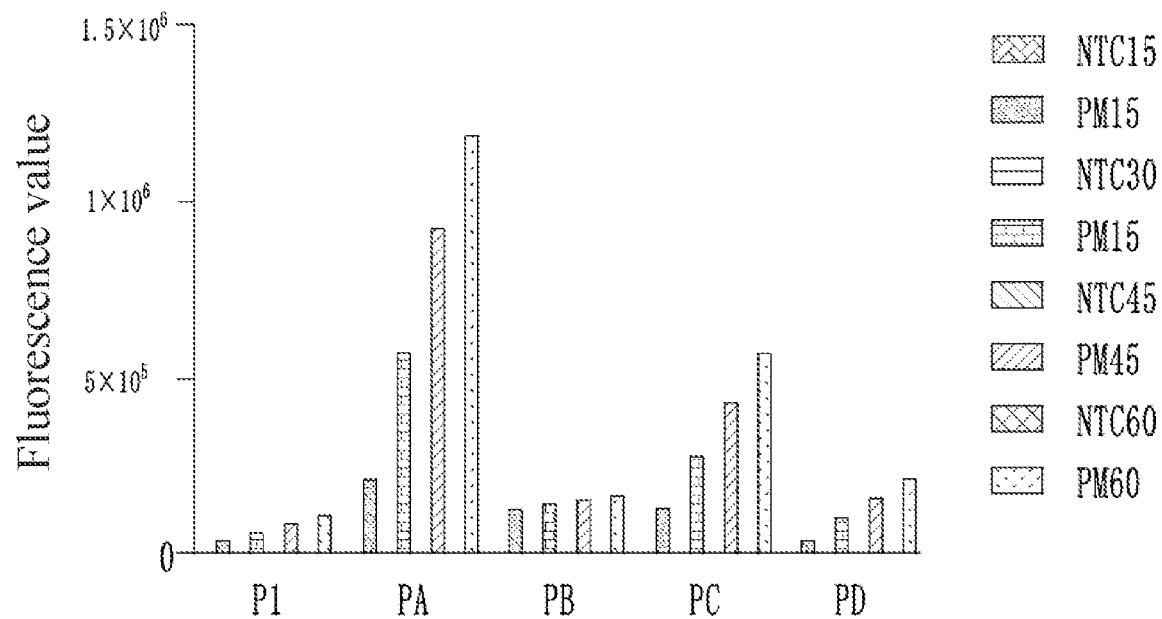
FIG. 1 shows the collateral cleavage activities of different ASFV P1192R sgRNAs.

A targeting sequence containing the Cas12b recognition sequence (PAM) 5'-TTN is searched for the P1192R gene fragment of ASFV, and sgRNAs of 20 bp are designed. These sgRNAs are named ASFV P1192R sgRNA P1, ASFV P1192R sgRNA PA, ASFV P1192R sgRNA PB, ASFV P1192R sgRNA PC, and ASFV P1192R sgRNA PD (hereinafter abbreviated as P1, PA, PB, PC, and PD), and their corresponding nucleic acid sequences are SEQ. ID NO: 1 to SEQ ID NO: 5, respectively.

The present disclosure provides a kit for detecting an ASFV based on the LAMP-CRISPR/Cas12b, including: a single guide RNA (sgRNA) targeting an ASFV P1192R gene, a loop-mediated isothermal amplification (LAMP) amplification primer designed for the ASFV P1192R gene, AapCas12b, a single-stranded DNA (ssDNA) probe, a Bst2.0 polymerase, and a reaction buffer; where the sgRNA has a nucleic acid sequence shown in any one of SEQ ID NO: 1 to SEQ ID NO: 5.

For the P1192R genes of popular strains ASFV type I and ASFV type II, the SNP sites are determined through sequence comparison, and then suitable primers are designed and selected through the online web page http://primerexplorer.jp/e/.

Preferably, the sequences of the LAMP primer set SET1 are shown in SEQ ID NO: 8 to SEQ ID NO: 11 in Table 1.

TABLE 1

Primer sequences of LAMP

| Grouping | Primer name | Sequence 5'-3' | Sequence ID |
|---|---|---|---|
| SET1 | F3 | AGGCTTACAAGCTGGATGC | SEQ ID NO: 8 |
|  | B3 | AGGAGCCYGGGTAATACTGG | SEQ ID NO: 9 |
|  | FIP | GCTAAAATTTTGCGCCGCGC-CCATCGAGCGGCAGATTCC | SEQ ID NO: 10 |
|  | BIP | AAGGTTTTTCAGTTCGGGGGCT-TGTTTAACGACATGTCGCCA | SEQ ID NO: 11 |

The reaction buffer includes MgSO$_4$ and betaine.

Preferably, MgSO$_4$ is used at a final concentration of 6 mM to 12 mM; more preferably, the MgSO$_4$ is used at a final concentration of 8 mM.

Preferably, the betaine is used at a final concentration of 0.1 M to 0.8 M; more preferably, the betaine is used at a final concentration of 0.5 M.

In the kit, the ssDNA probe has a sequence of optionally 5'-6-FAM-TTTTTTTTTTTT-BHQ1-3' shown in SEQ ID NO: 7.

A method for using the kit includes: mixing the sgRNA, the LAMP amplification primer, the AapCas12b, the ssDNA probe, the Bst2.0 polymerase, and the reaction buffer in the kit with a template to be tested to allow a reaction at a constant temperature of 55° C. to 60° C. for 30 min, and then reading an obtained reaction result through a fluorescence reading device.

Optionally, the kit further includes an immune colloidal gold test strip; and the ssDNA probe has a sequence of 5'-6-FAM-TTTTTTTTTTTT-Bio-3' shown in SEQ ID NO: 7.

The immune colloidal gold test strip is a lateral flow test strip; a conjugate pad includes a gold-labeled antibody capable of specifically binding to FAM; a test line is coated with an antibody, a protein, or avidin that is capable of binding to Bio; and a control line is coated with an antibody, a protein, or avidin that is capable of binding to the FAM.

A method for using the kit includes: mixing the sgRNA, the LAMP amplification primer, the AapCas12b, the ssDNA probe, the Bst2.0 polymerase, and the reaction buffer in the kit with a template to be tested to allow a reaction at a constant temperature of 55° C. to 60° C. for 30 min, and then adding an obtained reaction solution onto the immune colloidal gold test strip to allow color development.

Figure 9:
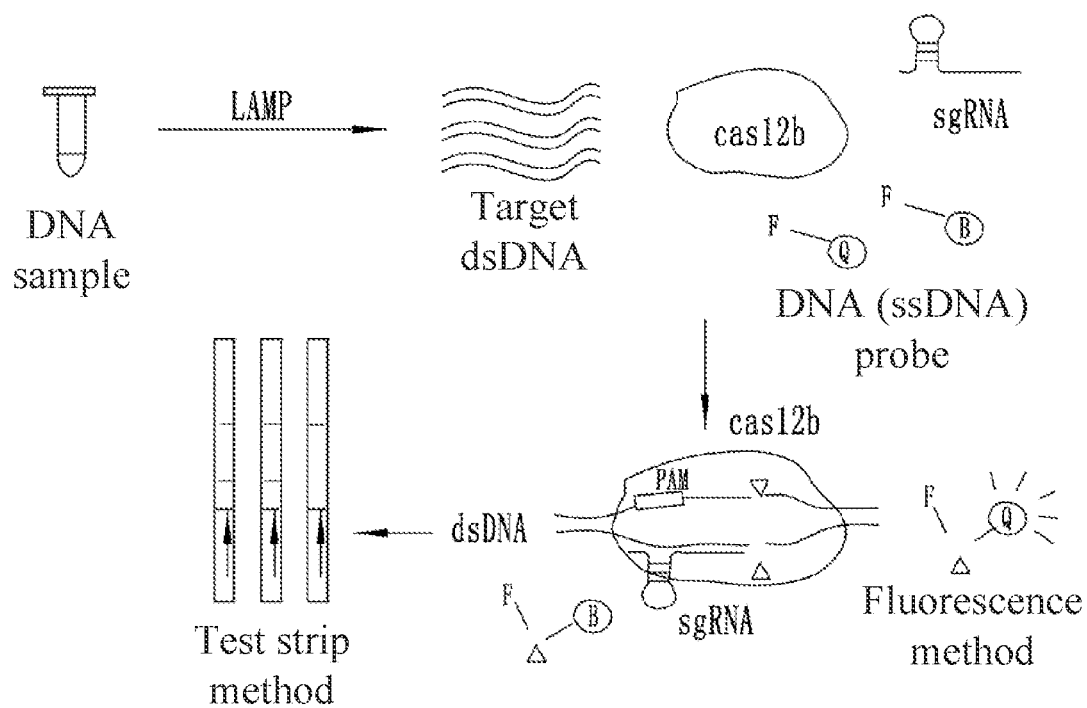
FIG. 9 shows a flow chart of the detection principle after the one-step nucleic acid detection is integrated with the immune colloidal gold test strip.

In the present disclosure, the detection principle of the constructed one-step nucleic acid detection method after fusion with the immune colloidal gold test strip is shown in FIG. 9. LAMP and Cas12b cleavage react simultaneously in one step, and a detection signal is amplified through isothermal amplification and probe cleavage twice to achieve the detection of low-abundance ASFV nucleic acid. This combined method can not only determine the result using signal intensity collected by the fluorescence method, but also directly visually observe the band changes of the test strip to quickly and accurately diagnose ASF.

In the present disclosure, unless otherwise specified, all raw material components are commercially available products well known to persons skilled in the art.

The technical solutions of the present disclosure will be clearly and completely described below with reference to the examples of the present disclosure. Apparently, the described examples are merely a part rather than all of the examples of the present disclosure. All other embodiments obtained by those skilled in the art based on the embodiments of the present disclosure without creative efforts shall fall within the protection scope of the present disclosure.

Example 1

Verification of sgRNA Cleavage Efficiency:

sgRNA plasmid was constructed according to the sequences SEQ ID NO: 1 to SEQ ID NO: 5 and then phosphorylated and annealed. The plasmid was linearized by EcoRI single enzyme digestion. A plasmid template DNA was extracted and purified using phenol: chloroform, and the sgRNA was obtained through in vitro transcription using T7 promoter. A 651 bp sequence of the P1152 sequence was directly synthesized as shown in SEQ ID NO: 6, and directly ligated with a pUC57 vector to form a pUC57-ASFV-P1192R plasmid. The primers for the ASFV P1192R target DNA fragment were designed and amplified. 200 ng of a recovered and purified target DNA fragment was mixed with 250 nM of Aapcas12b protein, 250 nM of ssDNA probe, and 200 nM of the sgRNA, and then reacted in an ABI 7500 fluorescence quantitative PCR instrument at a constant temperature of 60° C. for 2 h, and fluorescence was detected every 2 min to verify a cleavage efficiency.

The P1192R had a sequence shown in SEQ ID NO: 6.

The results were shown in FIG. 1, where NTC represented negative samples, PM represented positive samples, 15, 30, 45, and 60 represented 4 different time periods (15 min to 60 min) respectively, and P1, PA, PB, PC, and PD represented different sgRNAs. It was seen that sgRNA PA exhibited an extremely strong collateral cleavage activity, and the cleavage efficiency increased with time.

Example 2

Research on Cleavage Efficiency Under Different $MgSO_4$ Concentrations:

According to the operation method in Example 1, the cleavage activities of different sgRNAs in the presence of 6 mM to 12 mM $MgSO_4$ were explored. The recovered product of the amplified target DNA fragment was used as a template, and additional different concentrations of $MgSO_4$ were added to the LAMP buffer system containing 2 mM $MgSO_4$, such that a final $MgSO_4$ concentration of the reaction system was maintained at 6 nM to 12 mM. The fluorescence value was detected by ABI 7500 fluorescence quantitative PCR instrument to verify the collateral cleavage of 5 P1192R sgRNAs and Aapcas12b on the target fragment after cleavage.

Figure 2:
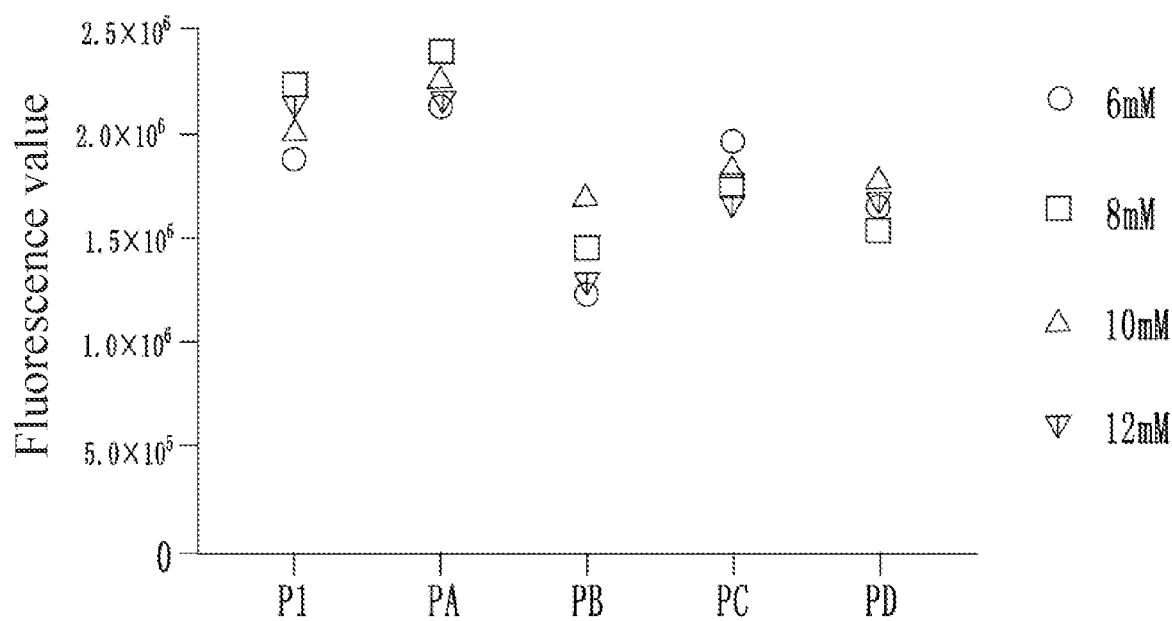
FIG. 2 shows collateral cleavage activity at different $MgSO_4$ concentrations.
Figure 3A:
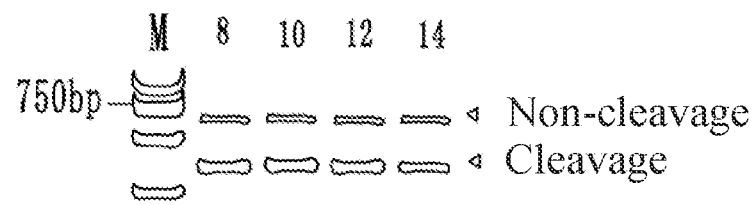
FIGS. 3A-3E show the enzyme digestion of a template DNA with betaine added at different $MgSO_4$ concentrations.
Figure 3B:
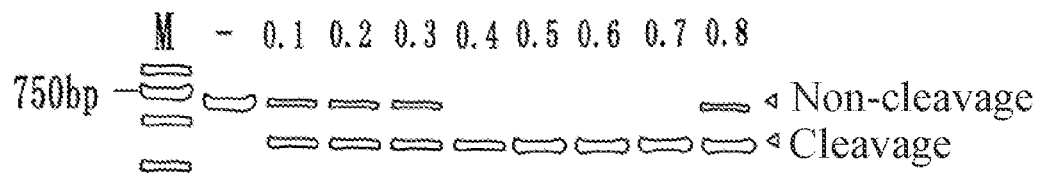
Figure 3C:
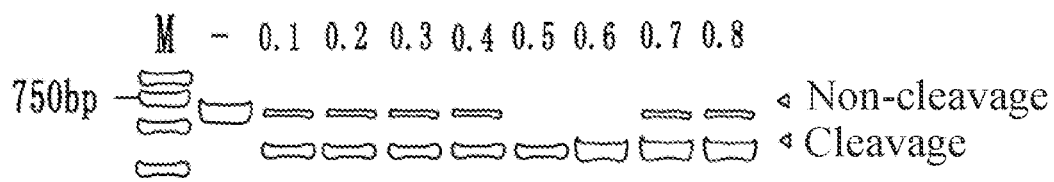
Figure 3D:
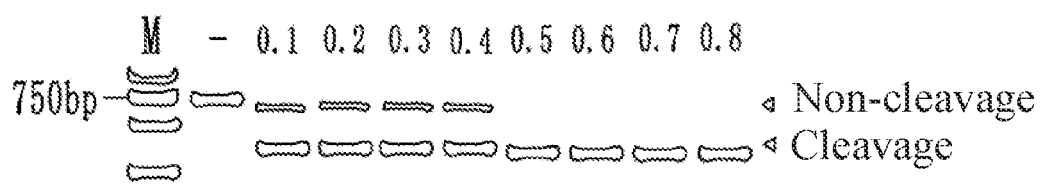
Figure 3E:
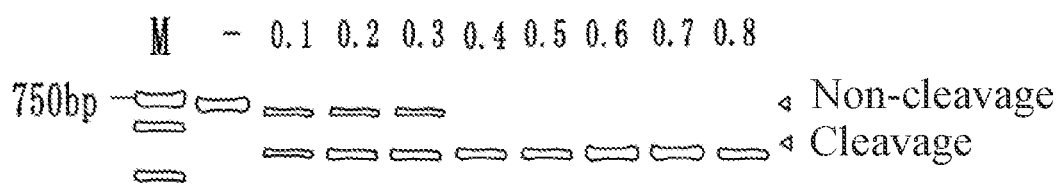

The results were shown in FIG. 2: P1, PA, PB, PC, and PD represented different sgRNAs; different sgRNAs under different $MgSO_4$ concentrations had different optimal cleavage activities; the optimal $MgSO_4$ concentration of PA was 8 mM, and the cleavage activity of PI was second only to that of PA.

Example 3

On the basis of Example 2, the recovered product of the target DNA fragment was used as a template. Additional different concentrations of $MgSO_4$ were added to the LAMP buffer system containing 2 mM $MgSO_4$ to maintain the final concentration of $MgSO_4$ at 8 mM to 14 mM. At the same time, there was no ssDNA probe, and additional 0.1 M to 0.8 M of betaine was added. Through agarose gel electrophoresis, the cleavage effect of sgRNA PA and Aapcas12b was explored on target fragments with different concentrations of betaine and $MgSO_4$.

The results were shown in FIGS. 3A-3E, where a was the cleavage at different $MgSO_4$ concentrations (8 mM to 14 mM); b was the cleavage when $MgSO_4$ concentration was 8 mM and different concentrations of betaine (0.1 M to 0.8 M) were added; c was the cleavage when $MgSO_4$ concentration was 10 mM and different concentrations of betaine (0.1 M to 0.8 M) were added; d was the cleavage when $MgSO_4$ concentration was 12 mM and different concentrations of betaine (0.1 M to 0.8 M) were added; e was the cleavage when $MgSO_4$ concentration was 14 mM and different concentrations of betaine (0.1 M to 0.8 M) were added.

It was seen that when betaine was added to the $MgSO_4$ system at different concentrations, it was found that betaine had a certain auxiliary cleavage effect. In the presence of 8 mM to 10 mM $MgSO_4$, adding an additional 0.5 M betaine to the system could completely cleave the template at a concentration of 200 ng.

Example 4

Cleavage Activity of the sgRNA Detected by One-Step Nucleic Acid Detection:

An optimized LAMP reaction system was used, including: 1×Isothermal Amplification Buffer, $MgSO_4$ 8 mM, dNTP Mix 0.5 mM, FIP/BIP Primers 0.64 μM, F3/B3 Primers 0.16 μM, Bst 2.0 DNA Polymerase 320 U/mL, Betaine 0.5 M, sgRNA 200 nM, Aapcas12b 250 nM, ssDNA probe 250 nM, and 200 ng concentration of template.

ssDNA probe was: 5'-6-FAM-TTTTTTTTTTTT-BHQ1-3'.

The LAMP primer set used SET1;

a pUC57-ASFV-P1192R plasmid was used as a positive control; and $ddH_2O$ was used as a negative control.

The isothermal amplification reaction system had a total volume of 20 μL, and was placed in an ABI 7500 fluorescence quantitative PCR instrument and reacted at a constant temperature of 60° C. for 2 h. Fluorescence was detected every 2 min.

Figure 4A:
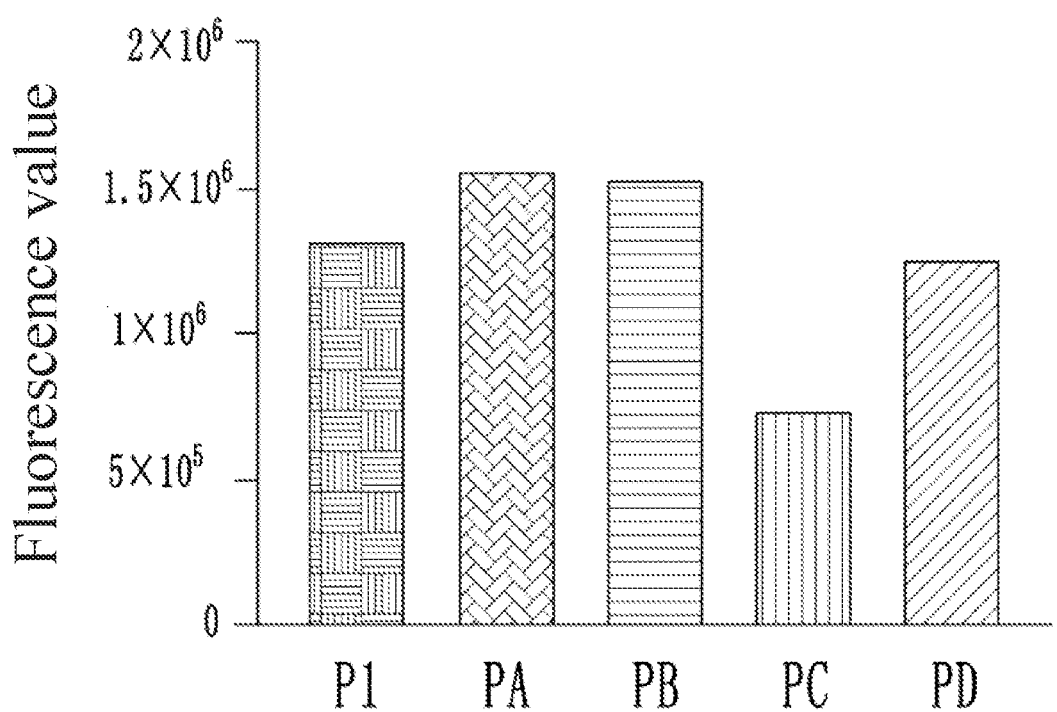
FIGS. 4A-4B show a cleavage activity of the sgRNA detected by one-step nucleic acid detection.
Figure 4B:
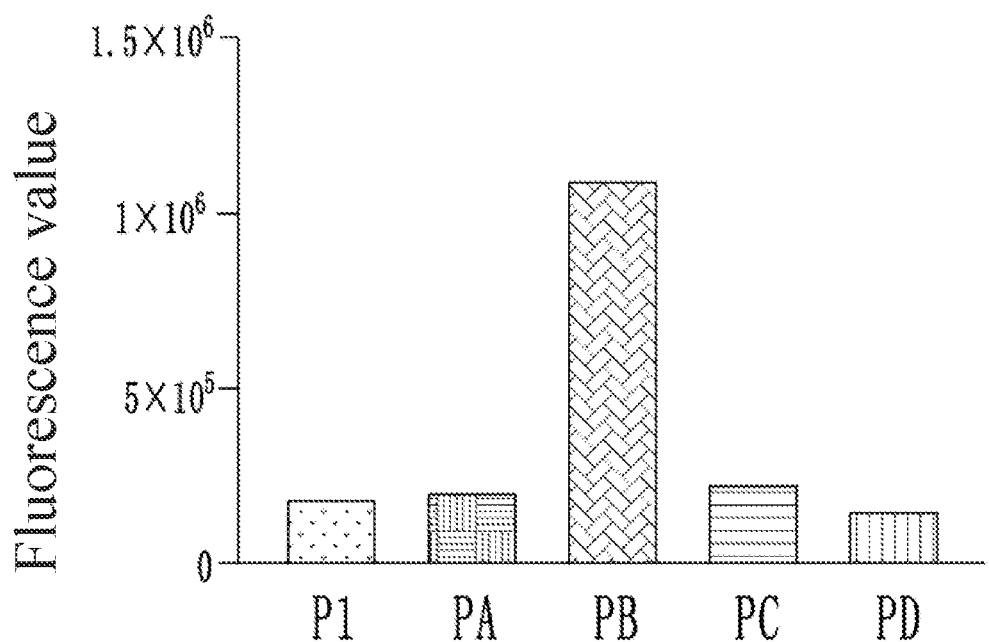

The results were shown in FIGS. 4A-4B, where the upper figure represented the positive results of different sgRNAs; while the lower figure represented the negative results of different sgRNAs. It was seen that P1, PA, PB, and PD had desirable cleavage reactions and showed varying degrees of cleavage efficiency, where PA had the highest cleavage activity. The fluorescence value of PC also appeared in the negative control amplification and cleavage reaction, but did not appear in the pure fluorescence cleavage of the fragment. This was related to the targeting LAMP primer, and PC was subsequently excluded.

Example 5

On the basis of the LAMP reaction system in Example 4, sgRNA-PA was used to explore the detection with different copy numbers of templates. A pUC57-ASFV-P1192R plasmid was used as a template, and the plasmid copy number was calculated. 10-fold gradient dilution was conducted to obtain plasmids containing $10^{10}$ to $10^0$ copies per microliter (copy/μL). 1 μL of gradient dilution plasmid template was added to the reaction system, and only the PA with the highest cleavage efficiency was selected as a crRNA. 20 μL of the total system was reacted in an ABI 7500 fluorescence quantitative PCR instrument at a constant temperature of 60° C. for 2 h, and fluorescence was detected every 2 min.

Figure 5:
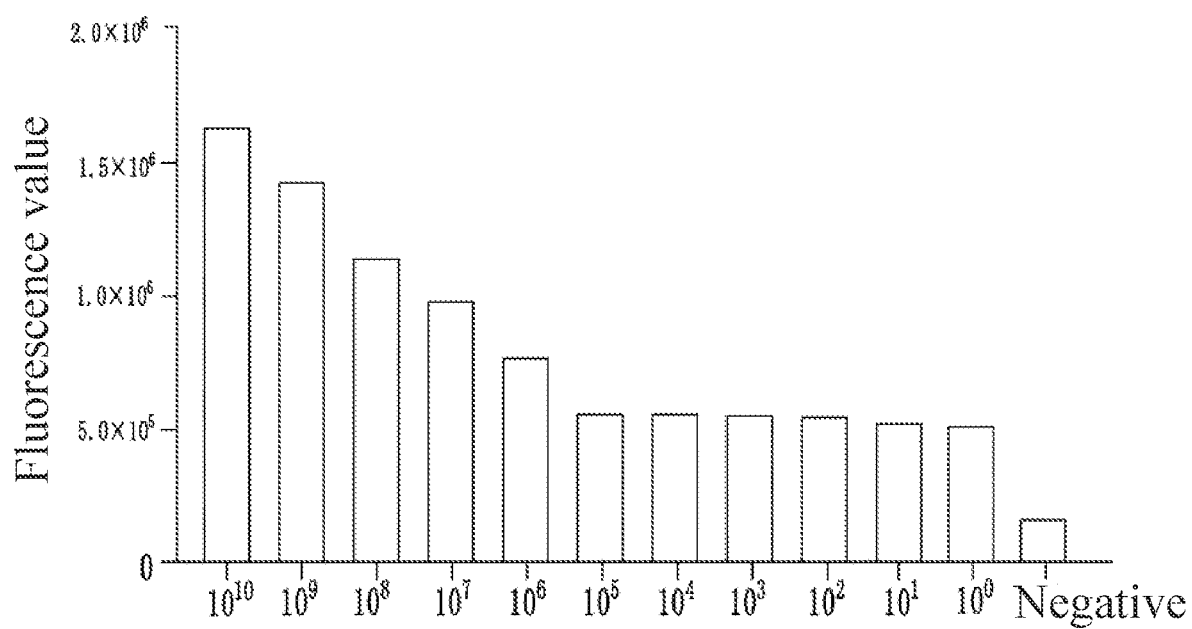
FIG. 5 shows the one-step nucleic acid detection results of plasmid templates with different copy numbers.

The results were shown in FIG. 5. For templates with different copy numbers, the fluorescence values of collateral cleavage activity showed the expected gradient amplification. The negative control results using water as a template showed that there was no amplification or cleavage during the entire reaction, and the lowest limit of detection could reach 1 copy/μL.

Example 6

Specific Detection Test:

On the basis of the LAMP reaction system in Example 4, sgRNA-PA was used to explore the detection under different virus templates. The nucleic acids of common porcine viral pathogens (PEDV, PADV3, SPV, PRV, PCV3, and CSFV) were used as templates, the pUC57-ASFV-P1192R plasmid was used as a positive control, which were added into an optimized 20 μL one-step reaction system. The system was reacted in an ABI 7500 fluorescence quantitative PCR instrument at a constant temperature of 60° C. for 2 h, and fluorescence was detected every 2 min.

Figure 6:
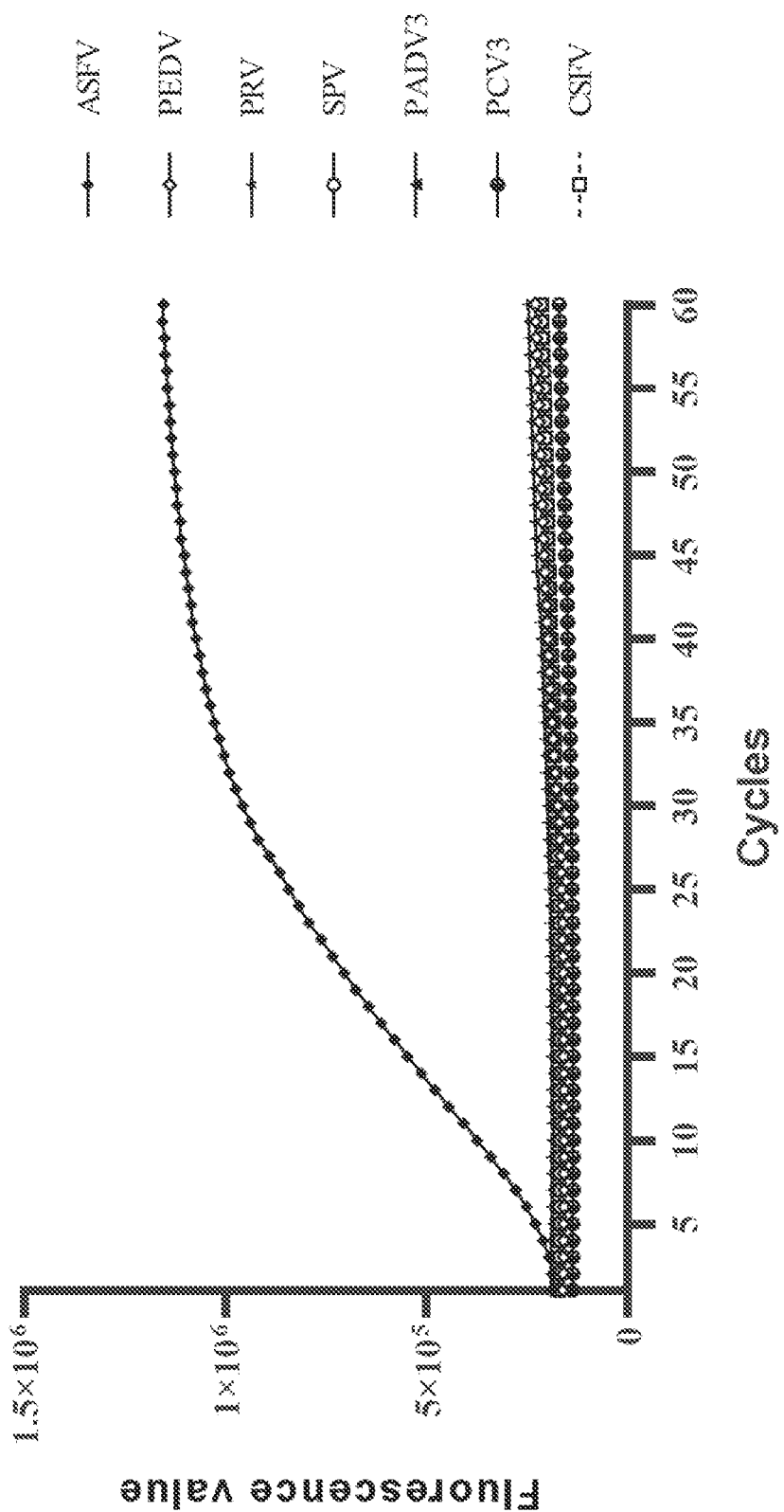
FIG. 6 shows the specificity evaluation results of the one-step nucleic acid detection.

The results were shown in FIG. 6, where PEDV was porcine epidemic diarrhea virus, PRV was pseudorabies virus, SPV was swine pox virus, PADV3 was porcine adenovirus type 3, PCV3 was porcine circovirus type 3, and CSFV was classical swine fever virus. It was seen that when other pig pathogens were used as templates for verification, the results were negative, which was the same as water as the template, and no amplification curve appeared, indicating that the detection method of the present application had a strong specificity.

Example 7

Clinical Sample Detection:

Clinical sample detection was completed by the African Swine Fever Regional Laboratory of China (Guangzhou) of South China Agricultural University, including 70 serum samples collected from ASFV-infected pig farms. There were 50 positive samples and 20 negative samples. The ASFV clinical serum samples were treated by a PBS boiling method, as follows: 50 µL of the serum was premixed with 200 µL of the PBS and boiled for 10 min, centrifuged at 12,000 rpm for 5 min, and a retained supernatant was aliquoted and stored at −20° C. qPCR was conducted in accordance with GB/T 18648-2020, which was mainly a fluorescence PCR method targeting the ASFV p72 (B646L) gene. Each sample was repeated 3 times. After adding the template, the 96-well qPCR plate was sealed and centrifuged briefly. The reaction plate was placed in the ABI 7500 fluorescence quantitative PCR instrument and the collected fluorescence signals were analyzed. At the same time, the LAMP reaction system of Example 4 and the selected sgRNA PA with higher cleavage activity were fused into one tube and reacted at a constant temperature of 60° C. for 40 cycles, with one cycle every 2 min, and then placed in an ABI 7500 fluorescence quantitative PCR instrument for evaluation of the fluorescence value.

Figure 7A:
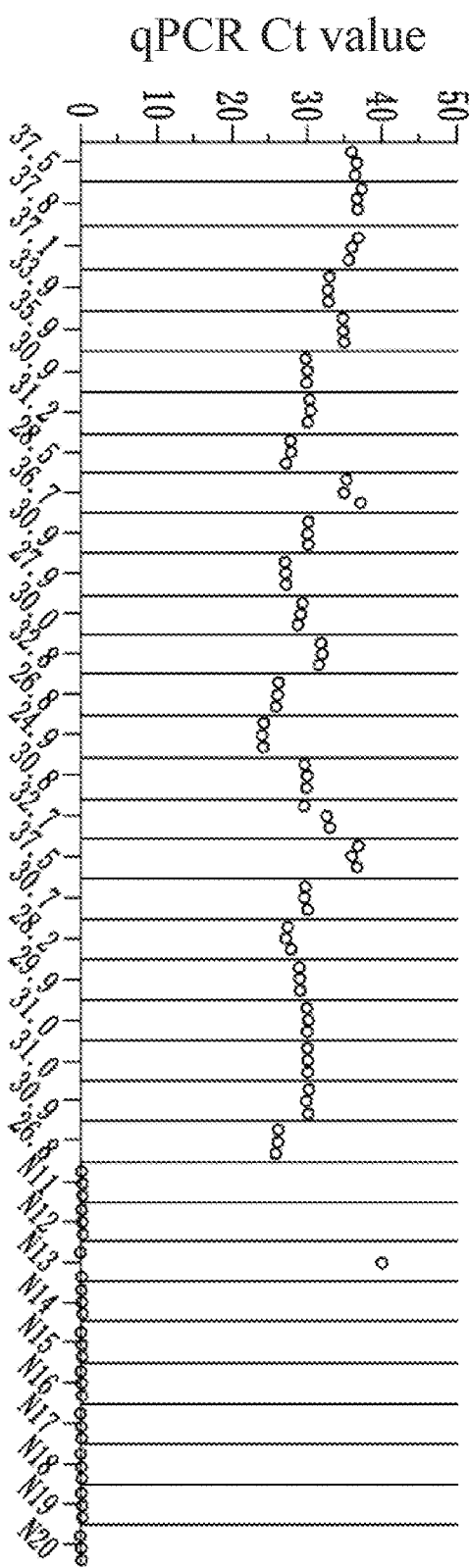
FIGS. 7A-7B show qPCR detection of clinical serum samples.
Figure 7B:
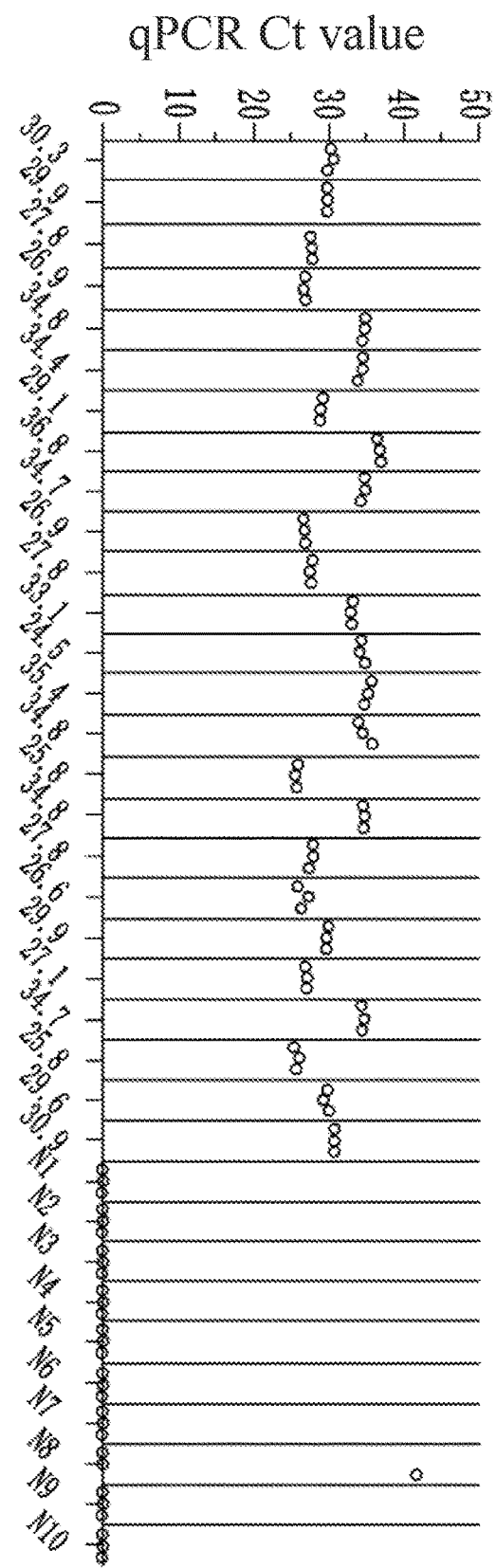
Figure 8:
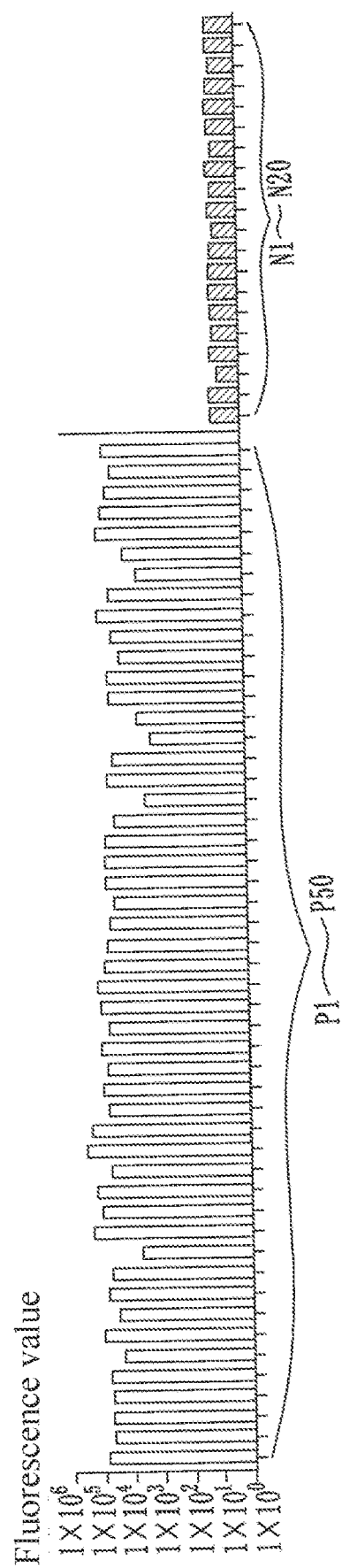
FIG. 8 shows the one-step nucleic acid detection results of clinically positive (P) and negative (N) serum samples.

FIGS. 7A-7B showed the Ct values detected by qPCR for 70 samples; while the results of nucleic acid detection using the optimized one-step method were shown in FIG. 8. The fluorescence cleavage value of positive serum samples was 103 to 106, and the background fluorescence value of negative results was 101. The fluorescence detection results of 50 positive samples and 20 negative samples were completely consistent with the fluorescence quantitative PCR detection results of same (Table 2), indicating that the method could be suitable for clinical diagnosis.

TABLE 2

Compliance between qPCR and one-step nucleic acid detection of clinical samples

| | | qPCR clinical serum sample detection | | | |
|---|---|---|---|---|---|
| | | Positive | Negative | Total | Predicted value |
| One-step nucleic acid detection | Positive | 50 (true positive) | 0 (false positive) | 50 | PPV = 100% |
| | Negative | 0 (false negative) | 20 (true negative) | 20 | NPV = 100% |
| | Total | 50 Sensitivity 100% | 20 Sensitivity 100% | 70 | |

Example 8

One-Step Nucleic Acid Detection & Immune Colloidal Gold Test Strip Combined with Naked Eye Visual Detection:

An amplification system in Example 4 was used, including: 1×Isothermal Amplification Buffer, $MgSO_4$ 8 mM, dNTP Mix 0.5 mM, FIP/BIP Primers 0.64µ, F3/B3 Primers 0.16µ M, Bst 2.0 DNA Polymerase 320 U/mL, Betaine 0.5 M, sgRNA 200 nM, Aapcas12b 250 nM, and ssDNA probe 250 nM.

ssDNA probe was: 5'-6-FAM-TTTTTTTTTTTT-Bio-3'.

The positive samples were: some of the 50 positive samples in Example 7;

the negative samples were: some of the 20 negative samples in Example 7; and

The isothermal amplification procedure is the same as the example, and the reaction was conducted in a constant-temperature metal bath at 60° C. for 40 min.

The immune colloidal gold test strip was HybriDetect (product number: MGHD1) from Milenia Biotec.

After amplification, fluorescent cleavage detection was not conducted, and the HybriDetect assay buffer and reaction solution were diluted at a ratio of 4:1, and 20 µL of a resulting mixture was pipetted into one side of the sample pad. After 10 min, the positive and negative results were determined directly through naked eye visualization (test paper settings in this application were different from the conventional ones: the one close to the sample adding end was set as a C line, while the one far away from the sample adding end was set as a T line). The results showed that after the test strip reacted for about 10 min, the positive sample showed two obvious bands, representing the control line (C line) and the test line (T line), respectively; while in the negative sample, only the C line appeared as a band.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A kit for detecting an African swine fever virus (ASFV), comprising:
   a single guide RNA (sgRNA) targeting an ASFV P1192R gene, a loop-mediated isothermal amplification (LAMP) amplification primer designed for the ASFV P1192R gene, AapCas12b, a single-stranded DNA (ssDNA) probe, a polymerase, and a reaction buffer; and further comprising an immune colloidal gold test strip; wherein
   the sgRNA has a nucleic acid sequence shown in SEQ ID NO: 2;
   the LAMP amplification primer has a sequence selected from SEQ ID NO: 8 to SEQ ID NO: 11;
   the reaction buffer comprises $MgSO_4$ and betaine; and
   the immune colloidal gold test strip is a lateral flow test strip comprising:
   1) A conjugate pad comprising a gold-labeled antibody capable of specifically binding to carboxyfluorescein (FAM);
   2) A test line coated with an antibody, a protein, or avidin that is capable of binding to biotin; and
   3) A control line coated with an antibody, a protein, or avidin that is capable of binding to the FAM.

2. The kit according to claim 1, wherein the ssDNA probe has a sequence of 5'-6-FAM-TTTTTTTTTTTT-Bio-3' shown in SEQ ID NO: 7.

* * * * *

SEQUENCE LISTING

```
Sequence total quantity: 11
SEQ ID NO: 1              moltype = RNA  length = 20
FEATURE                   Location/Qualifiers
source                    1..20
                          mol_type = other RNA
                          organism = synthetic construct
SEQUENCE: 1
gggggctacg ttgcagatca                                              20
```

-continued

```
SEQ ID NO: 2            moltype = RNA   length = 20
FEATURE                 Location/Qualifiers
source                  1..20
                        mol_type = other RNA
                        organism = synthetic construct
SEQUENCE: 2
aacgacatgt cgccatggtg                                                  20

SEQ ID NO: 3            moltype = RNA   length = 20
FEATURE                 Location/Qualifiers
source                  1..20
                        mol_type = other RNA
                        organism = synthetic construct
SEQUENCE: 3
tgtttaacga catgtcgcca                                                  20

SEQ ID NO: 4            moltype = RNA   length = 20
FEATURE                 Location/Qualifiers
source                  1..20
                        mol_type = other RNA
                        organism = synthetic construct
SEQUENCE: 4
tatcaccatg gcgacatgtc                                                  20

SEQ ID NO: 5            moltype = RNA   length = 20
FEATURE                 Location/Qualifiers
source                  1..20
                        mol_type = other RNA
                        organism = synthetic construct
SEQUENCE: 5
cagatcacat gttttatcac                                                  20

SEQ ID NO: 6            moltype = DNA   length = 651
FEATURE                 Location/Qualifiers
source                  1..651
                        mol_type = other DNA
                        organism = synthetic construct
SEQUENCE: 6
gagtcggagt tgcgaaaaag agagctttgc accggcgtgg tgccgctcac cgaaacccag       60
acgcagtcca ttcatagtgt ccgacgaatt ccttgcagcc tgcatctgca agtagatacc      120
aaggcttaca agctggatgc catcgagcgg cagattccca acttcttaga cgggatgacg      180
cgggcgcggc gcaaaatttt agccgggggg gtgaaatgct tcgcctccaa caaccgtgaa      240
cgaaaggttt ttcagttcgg gggctacgtt gcagatcaca tgttttatca ccatggcgac      300
atgtcgttaa acacaagtat tataaaagcc gcccagtatt acccaggctc ctcccacctc      360
tatccggtat tcataggcat aggaagtttt ggctccaggc acctgggagg aaaggatgca      420
ggatccccaa gatacatcag tgtgcagctt gcgtctgaat ttattaaaac aatgttcccc      480
gcggaggact catggcttct cccctacgtc tttgaggacg gccagcgggc ggaaccagag      540
tactacgtgc ctgtgttgcc gcttgctatt atggagtacg gcgccaaccc atcggagggc      600
tggaagtaca ccacttgggc ccggcaactg gaagacattt tggccttggt g              651

SEQ ID NO: 7            moltype = DNA   length = 12
FEATURE                 Location/Qualifiers
source                  1..12
                        mol_type = other DNA
                        organism = synthetic construct
SEQUENCE: 7
tttttttttt tt                                                          12

SEQ ID NO: 8            moltype = DNA   length = 19
FEATURE                 Location/Qualifiers
source                  1..19
                        mol_type = other DNA
                        organism = synthetic construct
SEQUENCE: 8
aggcttacaa gctggatgc                                                   19

SEQ ID NO: 9            moltype = DNA   length = 20
FEATURE                 Location/Qualifiers
source                  1..20
                        mol_type = other DNA
                        organism = synthetic construct
SEQUENCE: 9
aggagccygg gtaatactgg                                                  20

SEQ ID NO: 10           moltype = DNA   length = 39
FEATURE                 Location/Qualifiers
source                  1..39
                        mol_type = other DNA
                        organism = synthetic construct
```

```
SEQUENCE: 10
gctaaaattt tgcgccgcgc ccatcgagcg gcagattcc                              39

SEQ ID NO: 11           moltype = DNA  length = 42
FEATURE                 Location/Qualifiers
source                  1..42
                        mol_type = other DNA
                        organism = synthetic construct
SEQUENCE: 11
aaggtttttc agttcggggg cttgtttaac gacatgtcgc ca                          42
```